United States Patent [19]

Durant et al.

[11] 4,153,793
[45] May 8, 1979

[54] IMIDAZO ALKYLAMINO PYRIMIDONES

[75] Inventors: Graham J. Durant, Welwyn Garden City; John C. Emmett, Codicote; Charon R. Ganellin, Welwyn Garden City, all of England

[73] Assignee: Smith Kline & French Laboratories Limited, Welwyn Garden City, England

[21] Appl. No.: 778,812

[22] Filed: Mar. 17, 1977

Related U.S. Application Data

[62] Division of Ser. No. 619,724, Oct. 6, 1975, Pat. No. 4,035,374, which is a division of Ser. No. 463,647, Apr. 24, 1974, Pat. No. 3,932,644.

[30] Foreign Application Priority Data

May 3, 1973 [GB] United Kingdom ............... 21063/73
Jul. 26, 1973 [GB] United Kingdom ............... 35551/73

[51] Int. Cl.$^2$ .......................................... C07D 239/42
[52] U.S. Cl. ..................................... 544/320; 424/251
[58] Field of Search ................ 260/256.5 R, 256.4 R; 544/320

[56] References Cited

U.S. PATENT DOCUMENTS

| 3,894,151 | 7/1975 | Black et al. ........................... 424/246 |
| 3,923,809 | 12/1975 | Loev .............................. 260/256.5 R |

FOREIGN PATENT DOCUMENTS 473920 5/1951 Canada ..................................... 544/330

OTHER PUBLICATIONS

Burger, Medincinal Chemistry, 2nd Edition, (1960), p. 497.
Burger, Medincinal Chemistry, 3rd Edition (1970), p. 1588.

*Primary Examiner*—Donald G. Daus
*Assistant Examiner*—Lisa Jones
*Attorney, Agent, or Firm*—Joan S. Keps; Richard D. Foggio; William H. Edgerton

[57] ABSTRACT

Heterocyclic compounds which are inhibitors of histamine activity, in particular, inhibitors of H-2 histamine receptors. A specific compound of this invention is 2-[2-(4-methyl-5-imidazolylmethylthio)ethylamino]-4-pyrimidone.

7 Claims, No Drawings

IMIDAZO ALKYLAMINO PYRIMIDONES

This is a division of application Ser. No. 619,724 filed Oct. 6, 1975, now U.S. Pat. No. 4,035,374, which is a division of application Ser. No. 463,647 filed Apr. 24, 1974, now U.S. Pat. No. 3,932,644.

This invention relates to pharmacologically active compounds and pharmaceutical compositions and methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has recently been described by Black et. al. (Nature 1972, 236, 385) which are distinguished by the fact that they act at histamine receptors other than the H-1 receptor and these other receptors have been designated as H-2 receptors. This latter group of substances, to certain of which the present invention relates, are thus of utility in inhibiting certain actions of histamine which are not inhibited by the above mentioned "antihistamines". The substances of this invention may also be of utility as inhibitors of certain actions of gastrin.

Throughout the present specification, by the term "lower alkyl" we mean an alkyl group containing from 1 to 4 carbon atoms.

The compounds with which the present invention is concerned may be represented by the following general formula;

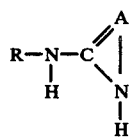

FORMULA I wherein A taken together with the nitrogen and carbon atoms shown forms a pyrimidine, imidazoline, quinazoline, pyridine, benzothiadiazine, 1,2,4-thiadiazine, thiazoline, 1,2,4-triazine or quinoline ring, said ring having a keto, thione or sulfone group and optionally substituted by one or two lower alkyl, phenyl or benzyl groups; R is a grouping of the structure shown in Formula II;

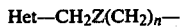
Het—CH$_2$Z(CH$_2$)$_n$—     FORMULA II wherein Het is a nitrogen containing heterocyclic ring such as imidazole, pyridine, thiazole, isothiazole or thiadiazole which ring is optionally substituted by lower alkyl preferably methyl, amino, hydroxy or halogen; Z is sulphur or a methylene group; and n is 2 or 3, or a pharmaceutically acceptable acid addition salt thereof.

It will be understood that, since the ring structures formed are potentially tautomeric systems, the Formula I shown is only one of several possible representations.

Particularly important classes of compounds which fall within the scope of Formula I are the compounds of the following Formulae III to VI:

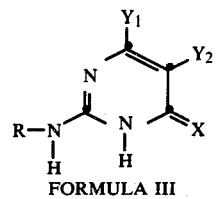 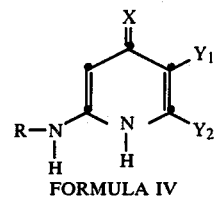
FORMULA III      FORMULA IV

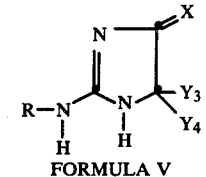 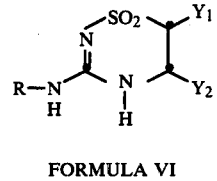
FORMULA V      FORMULA VI

Wherein R has the same significance as in Formula I, X is oxygen or sulphur; Y$_1$ and Y$_2$, which may be the same or different, are hydrogen, lower alkyl, phenyl or benzyl or Y$_1$ and Y$_2$ together with the adjacent carbon atoms may form a phenyl ring; and Y$_3$ and Y$_4$ which may be the same or different, are hydrogen, lower alkyl, phenyl or benzyl.

Particularly useful compounds of formulae I and III to VI are those wherein Het is imidazole, optionally substituted by methyl. It is also preferred that n should be 2.

Specific compounds of this invention having advantageous utility are:

2-[2-(4-methyl-5-imidazolylmethylthio)ethylamino]-4-pyrimidone,
2-[2-(4-methyl-5-imidazolylmethylthio)ethylamino]-5-ethyl-6-methyl-4-pyrimidone,
2-[2-(4-methyl-5-imidazolylmethylthio)ethylamino]-5-benzyl-6-methyl-4-pyrimidone,
2-[2-(4-methyl-5-imidazolylmethylthio)ethylamino]-(1H)-pyrid-4-one and
3-[2-(4-methyl-5-imidazolylmethylthio)ethylamino]-5,6-dihydro-1,2,4-thiadiazine-1,1-dioxide.

The compounds of the present invention may be produced by the reaction of a compound of Formula VII or of Formula VIII:

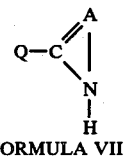 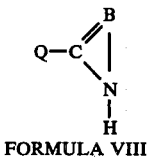
FORMULA VII      FORMULA VIII wherein A has the same significance as in Formula I, B is a chain of three or four atoms which are either all carbon atoms or which comprise a sulphur and/or one or two nitrogen atoms which chain also comprises a protected keto or thione grouping, and Q is a reactive grouping such as halogen, methanesulphonyl, thiol or alkylthio such as methylthio with an amino compound of formula R$^1$NH$_2$ wherein R$^1$ may have the same significance as R in Formula I or may be a group such that the product from its reaction with the compound of Formula VII or VIII may be converted by one or more reactions to a compound of Formula I.

As stated above, the compounds represented by Formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane at doses of from 2 to 256 micromoles per kilogram intravenously. Similarly, the action of these compounds may be demonstrated by their antagonism to the effects of histamine on other tissues which, according to the above-mentioned paper of Black et. al., are H-2 receptors. Examples of such tissues are perfused isolated guinea-pig heart, isolated guinea-pig right atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 2 to 256 micromoles per kilogram, given intravenously. Many of the compounds of the present invention produce a 50% inhibition in this test at a dose of from 5 to 20 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor.

Such addition salts include those with hydrochloric, hydrobromic, hydriodic, sulphuric and maleic acids and may conveniently be formed from the corresponding base by treatment of the latter with a dilute solution of the appropriate acid followed by recrystallisation from a suitable solvent such as aqueous ethanol.

Pharmaceutical compositions comprising a pharmaceutical carrier and a compound of formula I or a pharmaceutically acceptable acid addition salt thereof and methods of inhibiting H-2 histamine receptors which comprise administering a compound of formula I or a pharmaceutically acceptable acid addition salt thereof are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg to about 250 mg most preferably from about 100 mg to about 200 mg.

The active ingredient will preferably be administered in equal doses one to three times per day. The daily dosage regimen will preferably be from about 150 mg to about 750 mg most preferably from about 300 mg to about 600 mg.

Other pharmacologically active compounds may in certain cases be included in the composition. Advantageously the composition will be made up in a dosage unit form appropriate to the desired mode of administration, for example as a tablet, capsule or injectable solution.

The invention is illustrated but in no way limited by the following examples:

EXAMPLE 1

2-[2-(4-Methyl-5-imidazolylmethylthio)ethylamino]-4-pyrimidone dihydrochloride

An intimate mixture of 4(5)-(2-aminoethyl)thiomethyl-5(4)-methylimidazole (2.6 g) and 2-methylthio-4-pyrimidone (1.4 g) was heated to 150° over a period of 30 minutes, and then at 150°–160° for 2 hours. After cooling, the reaction mixture was triturated under water to give the crude base, which was filtered off and dissolved in 5N hydrochloric acid. Evaporation to dryness followed by recrystallisation of the residue from aqueous ethanol gave 2-[2-(4-methyl-5-imidazolylmethylthio)ethylamino]-4-pyrimidone dihydrochloride (2.1 g), m.p. 246°–248°.

(Found: C, 39.25; H, 5.2; N, 20.4; S, 9.6; Cl, 20.5; $C_{11}H_{17}Cl_2N_5OS$ requires: C, 39.1; H, 5.1; N, 20.7; S, 9.5; Cl, 20.95)

Recrystallisation of the initial crude base from ethanol/water gave the pure base, m.p. 219°–221°.

EXAMPLE 2

2-[2-(4-Methyl-5-imidazolylmethylthio)ethylamino]-6-methyl-4-pyrimidone dihydrochloride Reaction of 4(5)-[(2-aminoethyl)thiomethyl]-5(4)-methylimidazole (4.5 g.) with 6-methyl-2-methylthio-4-pyrimidone (2.7 g.) by the method described in Example 1 gave 2-[2-(4-methyl-5-imidazolylmethylthio)ethylamino]-6-methyl-4-pyrimidone dihydrochloride, m.p 247°–250° (ex ethanol).

(Found: C, 41.1; H, 5.7; N, 19.8; S, 8.9; Cl, 19.8; $C_{12}H_{19}Cl_2N_5OS$ requires: C, 40.9; H, 5.4; N, 19.9; S, 9.1; Cl, 20.1).

EXAMPLE 3

2-[2-(4-Methyl-5-imidazolylmethylthio)ethylamino]-5,6-dimethyl-4-pyrimidone dihydrochloride Reaction of 4(5)-(2-aminoethyl)thiomethyl-5(4)-methylimidazole (4.1 g.) with 5,6-dimethyl-2-methylthio-4-pyrimidone (2.6 g.) by the method described in Example 1 gave 2-[2-(4-methyl-5-imidazolylmethylthio)ethylamino]-5,6-dimethyl-4-pyrimidone dihydrochloride, m.p. 235°–237° (ex methanol).

(Found: C, 42.8; H, 6.0; N, 18.7; S, 8.6; Cl, 18.8; $C_{13}H_{21}Cl_2N_5OS$ requires: C, 42.6; H, 5.8; N, 19.1; S, 8.75; Cl, 19.4).

EXAMPLE 4

2-[4-(4-imidazolyl)butylamino]-4-pyrimidone dihydrochloride

Reaction of 4(5)-(4-aminobutyl)imidazole (2.1 g.) with 2-methylthio-4-pyrimidone (1.4 g.) by the method described in Example 1 gave 2-[4-(4-imidazolyl)butylamino]-4-pyrimidone dihydrochloride, m.p. 215°-222° (ex ethanol).

(Found: C, 43.15; H, 5.6; N, 22.5; Cl, 22.8; $C_{11}H_{17}Cl_2N_5O$ requires: C, 43.15; H, 5.6; N, 22.9; Cl, 23.2).

EXAMPLE 5

4-[2-(4-Methyl-5-imidazolylmethylthio)ethylamino]-2-thiopyrimidone dihydrochloride A solution of 4(5)-[(2-aminoethyl)thiomethyl]-5(4)-methylimidazole (7.4 g.) and 2,4-dimercaptopyrimidine (4.1 g.) in water (150 ml.) was heated under reflux for 12 hours. After cooling the precipitated oil was separated by decantation, washed with water (3×50 ml.), and dissolved in 2N hydrochloric acid. The solution was evaporated to dryness and the residue recrystallised from ethanol to give 4-[2-(4-methyl-5-imidazolylmethylthio)ethylamino]-2-thiopyrimidone dihydrochloride, m.p. 254°-257°.

(Found: C, 37.2; H, 4.9; N, 19.7; S, 18.0; $C_{11}H_{17}Cl_2N_5S_2$ requires: C, 37.3; H, 4.8; N, 19.8; S, 18.1).

EXAMPLE 6

4-[2-(4-Methyl-5-imidazolylmethylthio)ethylamino]-2-pyrimidone

A solution of 4-[2-(4-methyl-5-imidazolylmethylthio)ethylamino]-2-thiopyrimidone dihydrochloride (1.0 g.) and chloracetic acid (0.35 g.) in water (5 ml.) was heated on a steam bath for 40 min. Concentrated hydrochloric acid (8 ml.) was then added, the solution heated under reflux for 2 hours, and then evaporated to dryness. The residual oil was dissolved in water (5 ml.) basified with ammonium hydroxide and the precipitate washed with hot water to give 4-[2-(4-methyl-5-imidazolylmethylthio)ethylamino]-2-pyrimidone, m.p. 249°-251°.

(Found: C, 49.5; H, 5.6; N, 26.3; S, 18.0; $C_{11}H_{15}N_5OS$ requires: C, 49.8; H, 5.7; N, 26.4; S, 18.1).

EXAMPLE 7

2-[2-(4-Methyl-5-imidazolylmethylthio)ethylamino]-2-imidazoline-4-one dihydrochloride.

A solution of 4(5)-(2-aminoethyl)thiomethyl-5-(4)-methylimidazole (3.4 g.) and 2-methylthio-2-imidazolin-4-one hydrochloride (2.6 g.) in dry ethanol (20 ml.) was left to stand at room temperature for 4 days. The crude product was filtered off, dissolved in dilute hydrochloric acid and the solution basified with aqueous potassium carbonate solution to give 2-[2-(4-methyl-5-imidazolylmethylthio)ethylamino]-2-imidazoline-4-one, m.p. 224°-5° (decomp.). The dihydrochloride, m.p. 226°-228° (decomp.) was obtained by dissolving the base in dilute hydrochloric acid, evaporating to dryness and recrystallising the residue from aqueous ethanol.

(Found: C, 31.1; H, 5.4; N, 21.45; S, 9.7; Cl, 21.6; $C_{10}N_{17}Cl_2N_5OS$ requires: C, 36.8; H, 5.25; N, 21.5; S, 9.8; Cl, 21.7).

EXAMPLE 8

2-[2-(4-Methyl)-5-imidazolylmethylthio)ethylamino]-4(1H)-quinazolinone

Reaction of an intimate mixture of 4(5)-(2-aminoethyl)thiomethyl-5(4)-methylimidazole (2.6 g.) with 2-methylthio-4(1H)-quinazolinone (1.9 g.) at 120° for 4½ hours gave the crude base (2.7 g.) which was acidified with hydrochloric acid as described in Example 1, to give, on recrystallisation from ethanol/ether, 2-[2-(4-methyl-5-imidazolylmethylthio)ethylamino]-4(1H)-quinazolinone dihydrochloride, m.p. 249°-252°.

(Found: C, 45.8; H, 4.9; N, 17.8; S, 8.1 $C_{15}H_{14}Cl_2N_5OS$ requires: C, 46.4; H, 4.9; N, 18.0; S, 8.3;).

EXAMPLE 9

2-[2-(4-Methyl-5-imidazolylmethylthio)ethylamino]-6-n-propyl-4-pyrimidone

Reaction of 4(5)-(2-aminoethyl)thiomethyl-5(4)-methylimidazole (5 g.) with 6-n-propyl-2-methylthio-4-pyrimidone (5 g.) by the method described in Example 1 gave a hygroscopic dihydrochloride of 2-[2-(4-methyl-5-imidazolylmethylthio)ethylamino]-6-n-propyl-4-pryimidone, m.p. 125°-130° (crystallised from butanol/ether).

(Found: C, 44.3; H, 6.2; N, 18.3; S, 8.2; Cl, 18.7. $C_{14}H_{23}Cl_2N_5OS$ requires: C, 44.2; H, 6.1; N, 18.4; S, 8.4; Cl, 18.6).

EXAMPLE 10

2-[2-(4-Methyl-5-imidazolylmethylthio)ethylamino]-5-ethyl-6-methyl-4-pyrimidone dihydrochloride Reaction of 4(5)-(2-aminoethyl)thiomethyl-5(4)-methylimidazole (2.0 g.) with 5-ethyl-6-methyl-2-methylthio-4-pyrimidone (1.46 g.) by the method described in Example 1 gave 2-[2-(4-methyl-5-imidazolylmethylthio)ethylamino]-5-ethyl-6-methyl-4-pyrimidone dihydrochloride m.p. 203°-7° (crystallised from isobutanol)

(Found: C, 43.6; H, 6.1; N, 17.9; S, 8.0; Cl, 18.5. $C_{14}H_{23}Cl_2N_5O_6$ requires: C, 44.2; H, 6.1; N, 18.5; S, 8.4; Cl, 18.6).

EXAMPLE 11

2-[2-(4-Methyl-5-imidazolylmethylthio)ethylamino]-5-methyl-2-imidazolin-4-one A solution of 5-methyl-2-thiohydantoin (15 g.) and methyl iodide (16.3 g.) in dry ethanol (130 ml.) was heated under reflux for 1½ hours, and then allowed to stand at 0° overnight. The crystalline product was filtered and washed with ether to give 2-methylthio-5-methyl-2-imidazolin-4-one hydroiodide (17.8 g.), m.p. 170°-173°.

A solution of this hydroiodide (2.7 g.), 4(5)-(2-aminoethyl) thiomethyl-5(4)-methylimidazole (2.5 g.) and triethylamine (1 g.) in dry ethanol (20 ml.) was left to stand at room temperature for 10 days. The resulting crude product (1.6 g., m.p. 218°) was dissolved in hydrochloric acid and the solution basified with saturated aqueous potassium carbonate solution to give hydrated 2-[2-(4-methyl-5-imidazolylmethylthio)ethylamino]-5-methylimidazolin-4-one, m.p. 216°-220°.

(Found: c, 48.5; H, 6.4; N, 25.4; S, 11.9. $C_{11}H_{17}N_5OS$ ½$H_2O$ requires: C, 48.3; H, 6.5; N, 25.6; S, 11.7).

EXAMPLE 12

5,5-Dimethyl-2-[2-(4-methyl-5-imidazolylmethylthio)-ethylamino]-2-imidazolin-4-one 5,5-Dimethyl-2-thiohydantion (14.4 g.) was converted to 2-methylthio-5,5-dimethyl-2-imidazolin-4-one hydroiodide (17.4 g., m.p. 187°–189°) according to the method described in Example 11. A solution of this hydroiodide (5.7 g.) and 4(5)-(2-aminoethyl)thiomethyl-5(4)-methylimidazole (6.85 g.) in dry ethanol (45 ml.) was left to stand at room temperature for 4 days. The reaction mixture was evaporated to dryness and the residue recrystallised from water to give 5,5-dimethyl-2-[2-(4-methyl-5-imidazolyl)methylthio)ethylamine]-2-imidazolin-4-one (3.1 g.) m.p. 232°–236°. Further recrystallisation from water gave an analytical sample, m.p. 235°–7°.

(Found: C, 50.9; H, 6.9; N, 24.8; S, 11.4; $C_{12}H_{19}N_5OS$ requires: C, 51.2; H, 6.8; N, 24.9; S, 11.4).

EXAMPLE 13

5-Benzyl-2-[2-(4-methyl-5-imidazolylmethylthio)ethylamino]-2-imidazolin-4-one 5-Benzyl-2-thiohydantoin was converted to 2-methylthio-5-benzyl-2-imidazolin-4-one hydroiodide (m.p. 192°–194°) according to the method described in Example 11.

A solution of this hydroiodide (2.5 g.), 4(5)-(2-aminoethyl)-thiomethyl-5(4)-methylimidazole (1.9 g.) and triethylamine (0.74 g.) in dry ethanol (15 ml.) was left to stand at room temperature for 4 days. The reaction mixture was evaporated to dryness, the residue dissolved in isopropanol (25 ml.) and the resulting solution poured into ether (200 ml.) to give 5-benzyl-2-[2-(4-methyl-5-imidazolylmethylthio)ethylamino]-2-imidazolin-4-one (1.23 g.) m.p. 104°–7°.

EXAMPLE 14

2-[2-(4-Methyl-5-imidazolylmethylthio)ethylamino]-pyrimid-4-thione dihydrochloride A mixture of 2-[2-(4-methyl-5-imidazolylmethylthio)ethylamino]-4-pyrimidone (5 g.) and phosphorus pentasulphide (4 g.) in pyridine (150 ml.) was heated under reflux, with stirring, for 2 hours. The reaction mixture was evaporated to dryness, boiled with water for 30 minutes and again evaporated to dryness. The residue was dissolved in dilute ammonium hydroxide, the solution washed with chloroform and the aqueous layer evaporated to dryness. Concentrated hydrochloric acid was added to the residue to give a pale yellow solid, which was dissolved in warm water, filtered, and the filtrate acidified with concentrated hydrochloric acid to give 2-[2-(4-methyl-5-imidazolylmethylthio)ethylamino]pyrimid-4-thione dihydrochloride, m.p. 245°–247°.

(Found: c, 37.0; H, 4.9; N, 19.55; S, 17.7; $C_{11}H_{17}Cl_2N_5S_2$ requires: C, 37.3; H, 4.8; N, 19.8; S, 18.1).

EXAMPLE 15

2-[2-(4-Methyl-5-imidazolylmethylthio)ethylamino]-(1H)-pyrid-6-one

A mixture of 4(5)-(2-aminoethyl)thiomethyl-5(4)-methylimidazole (20 g.) and 2-bromo-6-ethoxy-pyridine (11.9 g.) was heated with stirring at 160° for 4 hours. After cooling, the reaction mixture was dissolved in 20% aqueous hydrobromic acid and the solution extracted with ether to recover unchanged 2-bromo-6-ethoxypyridine. The aqueous layer was basified with potassium carbonate, extracted with chloroform and the combined extract washed with water and dried (MgSO$_4$). After removal of the chloroform the residue was chromatographed on silica gel, eluting with first ethyl acetate to remove impurities and then ethyl acetate/methanol/chloroform (4:1:2) to elute the required product. Evaporation of the eluate gave 2-ethoxy-6-[2-(4-methyl-5-imidazolylmethylthio)ethylamino]pyridine as an oil, which on treatment with a solution of picric acid in ethanol gave the dipicrate, m.p. 172°.

A solution of this ethoxypyridine (3.4 g. of base) in 5N hydrochloric acid (100 ml) was heated under reflux for 2½ hours. The reaction mixture was evaporated to dryness, the residue dissolved in a minimum amount of water, the solution basified with aqueous potassium carbonate, washed once with chloroform, and allowed to stand at 0° overnight. Crystals of 2-[2-(4-methyl-5-imidazolylmethylthio)ethylamino]-(1H)-pyrid-6-one were collected and recrystallised from water to give the pure product, m.p. 85°.

(Found: C, 54.25; H, 6.0; N, 20.9; S, 11.9. $C_{12}H_{16}N_4OS$ requires: C, 54.5; H, 6.1; N, 21.2; S, 12.1).

EXAMPLE 16

2-[2-(4-Methyl-5-imidazolylmethylthio)ethylamino]-(1H)-pyrid-4-one

A mixture of 4(5)-(2-aminoethyl)thiomethyl-5(4)-methylimidazole (7.6 g.) and 2-bromo-4-pyridone (3.8 g.) was heated with stirring at 160° for 3 hours. After cooling, the reaction mixture was chromatographed on silica gel, eluting with first ethyl acetate isopropanol (5:1) to remove unreacted 2-bromo-4-pyridone and then isopropanol/ethanol (5:1) to remove the product. After evaporation of the combined eluates the residue was purified further by ionexchange chromatography using IRA 400 (OH form) resin and eluting first with water to remove unchanged amine and then IN hydrochloric acid to remove the product. Evaporation of the acid fractions and recrystallisation of the residue from isopropanol/ethyl acetate gave 2-[2-(4-methyl-5-imidazolylmethylthio)ethylamino]-(1H)-pyrid-4-one, m.p. 208°–210°.

EXAMPLE 17

3-[2-((4-Methyl-5-imidazolylmethylthio)ethyl)amino]-1,2,4-benzothiadiazine-1,1-dioxide A mixture of 3-methylmercapto-1,2,4-benzothiadiazine-1,1-dioxide (5.58 g.) and 4-methyl-5-((2-aminoethyl)thiomethyl)imidazole (4.20 g.) was heated at 140°–150° for 2 hours and then cooled. Following dissolution in ethanol, and cooling the crude product was obtained as a solid (5.67 g.) which was recrystallised from water and then methanol to give 3-[2-((4-methyl-5-imidazolylmethylthio)ethyl)amino]-1,2,4-benzothiadiazine-1,1-dioxide (4.30 g.), m.p. 194.5°–196°.

(Found: C, 48.0; H, 5.0; N, 19.8; S, 18.2. $C_{14}H_{17}N_5O_2S_2$ requires: C, 47.8; H, 4.9; N, 19.9; S, 18.3).

EXAMPLE 18

3-[2-((4-Methyl-5-imidazolyl)methylthio)ethylamino]-5,6-dihydro-1,2,4-thiadiazine-1,1-dioxide A mixture of 4-methyl-5-((2-aminoethyl)thiomethyl)imidazole (4.0 g.) and 3-methylthio-5,6-dihydro-1,2,4- thiadiazine-1,1-dioxide (4.2 g.) was heated in an oil bath at 140° for 4 hours. The product was chromatographed on a column of silica gel with ethyl acetate-ethanol (3:2) as eluant and finally recrystallised from ethanol-ether to give 3-[2-((4-methyl-5-imidazolyl)methylthio)ethylamino]-5,6-dihydro-1,2,4-thiadiazine-1,1-dioxide (2.2 g.) m.p. 146°–147°.

(Found: C, 39.6; H, 6.0; N, 22.9. $C_{10}H_{17}N_5O_2S_2$ requires: C, 39.6; H, 5.7; N, 23.1).

EXAMPLE 19

4-[2-((4-Methyl-5-imidazolylmethylthio)ethylamino]-thiazoline-2-one

A solution of 4-methyl-5-[(2-aminoethyl)thiomethyl]imidazole (1.71 g.) and thiazolidine-2-one-4-thione (1.33 g.) in methanol (30 ml.) was heated under reflux for one hour. Concentration, followed by successive recrystallisation of the residue from methanol, ethanol and aqueous ethanol afforded 4-[2-(4-methyl-5-imidazolyl)methylthio) ethyamino]thiazoline-2-one (1.0 g.) m.p. 195°–197°.

(Found: C, 44.2; H, 5.1; N, 20.5; S, 23.6. $C_{10}H_{14}N_4OS_2$ requires: C,44.4; H, 5.2; N, 20.7; S, 23.7).

EXAMPLE 20

3-[2-(4-Methyl-5-imidazolylmethylthio)ethylamino]-6-methyl-1,2,4-triazin-2H-5-one An intimate mixture of 3-methylthio-6-methyl-1,2,4-triazin-2H-5-one (7.64 gms) and 5-(2-aminoethyl)thiomethyl-4-methylimidazole (8.75 gms) was heated slowly to 160° C. and maintained at this temperature for one hour. After cooling the resulting solid was dissolved in 2N.HCl (100 ml), filtered and the filtrate basified with aqueous $K_2CO_3$ solution. The resulting precipitate was collected, washed with water, dried and extracted in a Soxhlet extractor with methanol for 16 hours. The methanol solution was cooled giving yellow-buff crystals. Recrystallisation from dimethylsulphoxide gave 3-[2-(4-methyl-5-imidazolylmethylthio)ethylamino]-6-methyl-1,2,4-triazin-2H-5-one. (7.8 gms.), m.p. 264°–266° C. (Dec).

(Found: C, 46.8; H, 5.7; N, 29.9; S, 12.0; $C_{11}H_{16}N_6OS$ requires: C, 47.1; H, 5.7; N, 30.0; S, 11.44).

EXAMPLE 21

3-[2-(4-Methyl-5-imidazolylmethylthio)ethylamino]-1,2,4-triazin-2H-5-one

An intimate mixture of 5-(2-aminoethyl)thiomethyl-4-methyl imidazole (8.6 gms) and 3-methylthio triazin-2H-5-one (6.68 gms) was slowly heated to 120° C. and kept at this temperature for four hours. After cooling the resulting solid was recrystallised twice from n-propanol and twice from water to give 3-[2-(5-methyl-4-imidazolylmethylthio)ethylamio]-1,2,4-triazin-2H-5-one, m.p. 238°–238.5° C.

(Found: C, 45.1; H, 5.55; N, 31.5; S, 11.9; $C_{10}H_{14}N_6OS$ requires: C, 45.1; H, 5.3; N, 31.6; S, 12.0).

EXAMPLE 22

2-[2-(4-Methyl-5-imidazolylmethylthio)ethylamino]-5-benzyl-6-methyl-4-pyrimidone 5-Benzyl-6-methylthiouracil (6.0 gms) and sodium hydroxide (1.06 gms) were dissolved in water (30 mls). The solution was cooled and ethanol (60 mls) and methyl iodide (3.67 gms) added with stirring. The mixture was heated at 60° C. for ½ hour, cooled and the resulting solid collected and water-washed. A second crop of solid was obtained by acidification of the filtrate to pH=4 with acetic acid. Recrystallisation from ethanol produced 5-benzyl-6-methyl-2-methylthio-4-pyrimidone (5.53 gms) m.p.=220°–221.5° C.

An intimate mixture of 5-(2-aminoethyl)thiomethyl-4-methylimidazole (1.28 gms) and 5-benzyl-6-methyl-2-methylthio-4-pyrimidone (1.84 gms) was heated at 150°–160° C. (oil-bath temperature) for 4½ hours. The mixture was cooled, washed with water and recrystallised from isopropanol to give 2-[-2-(4-methyl-5-imidazolylmethylthio)ethylamino]-5-benzyl-6-methyl-4-pyrimidone (1.82 gms) m.p.=140°–141.5° C.

(Found: C, 61.7; H, 6.6; N, 18.5; S, 8.20; $C_{19}H_{23}N_5OS$ requires: C, 61.8; H, 6.3; N, 18.95; S, 8.68).

EXAMPLE 23

2-[2-(4-Methyl-5-imidazolylmethylthio)ethylamino]-4-quinolone

2-Chloro-4-ethoxyquinoline (3.72 gms) and 5-(2-aminoethyl)thiomethyl- 4-methylimidazole (3.1 g.) were heated together at 150°–160° C. (oil-bath temperature) for three hours. The residue, on colling, was washed with water and dried. Purification was effected by column chromatography (silica gel column, ethyl acetate-5% methanol eluant) and crystallisation from acetone to give 2-[2-(4-methyl-5-imidazolylmethylthio)ethylamino]-4-ethoxyquinoline (1.86 gms) m.p. 152.5°–153.5° C.

(Found: C, 63.2; H, 6.5; N, 16.1; S, 9.1. $C_{18}H_{22}N_4OS$ requires: C, 63.1; H, 6.5; N, 16.4; S, 9.4).

2-[2-(4-Methyl-5-imidazolylmethylthio)ethylamino]-4-ethoxyquinoline (1.69 gms) and concentrated HCl (30 mls) were refluxed together for 17 hours. The solution was evaporated to dryness, the residue dissolved in water and basified with potassium carbonate. The precipitated oil was separated by decantation, washed with water and crystallised from isopropanol-water to give 2[-2-(4-methyl-5-imidazolylmethylthio)ethylamino]-4-quinolone. m.p. 121°–124° C.

(Found: C, 60.1; H, 5.7; N, 17.1; S, 9.9; $C_{16}H_{18}N_4OS$ requires; C, 61.1; H, 5.8; N, 17.8; S, 10.2).

EXAMPLE 24

4-[4-(4-Imidazolyl)butylamino]-2-thiopyrimidone

Reaction of 4(5)-(4-aminobutyl)imidazole (2.8 g.) with 2,4-dimercaptopyrimidine (1.44 g.) by the method described in Example 5 gave 4-[4-imidazolyl)-butylamino]-2-thiopyrimidone, m.p. 209°–211° (ex n-propanol).

(Found: C, 51.4; H, 6.3; N, 27.0; S, 13.0 $C_{11}H_{15}N_5S$. 0.4 $H_2O$ requires: C, 51.6; H, 6.3; N, 27.35; S, 12.5).

EXAMPLE 25

Reaction of 2-methylthio-4-pyrimidone by the procedure of Example 1 with the following compounds:

4-[(2-aminoethyl)thiomethyl]imidazole
4-(2-aminoethyl)thiomethyl-5-bromoimidazole
4-[(3-aminopropyl)thiomethyl]imidazole
2-(2-aminoethyl)thiomethyl-3-bromopyridine
2-(2-aminoethyl)thiomethyl-3-hydroxypyridine
2-(2-aminoethyl)thiomethyl-3-methylpyridine
2-(2-aminoethyl)thiomethyl-3-aminopyridine
2-[(2-aminoethyl)thiomethyl]thiazole
2-(4-aminobutyl)thiazole
3-[(2-aminoethyl)thiomethyl]isothiazole 3-(2-aminoethyl)thiomethyl-4-bromoisothiazole
2-amino-5-(2-aminoethyl)thiomethyl-1,3,4-thiadiazole
4-(5-aminopentyl)imidazole yields the following products:
2-[2-(4-imidazolylmethylthio)ethylamino]-4-pyrimidone
2-[2-(4-bromo-5-imidazolylmethylthio)ethylamino]-4-pyrimidone
2-[3-(4-imidazolylmethylthio)propylamino]-4-pyrimidone
2-[2-(3-bromo-2-pyridylmethylthio)ethylamino]-4-pyrimidone
2-[2-(3-hydroxy-2-pyridylmethylthio)ethylamino]-4-pyrimidone
2-[2-(3-methyl-2-pyridylmethylthio)ethylamino]-4-pyrimidone
2-[2-(3-amino-2-pyridylmethylthio)ethylamino]-4-pyrimidone
2-[2-thiazolylmethylthio)ethylamino]-4-pyrimidone
2-[4-(2-thiazolyl)butylamino]-4-pyrimidone
2-[2-(3-isothiazolylmethylthio)ethylamino]-4-pyrimidone
2-[2-(4-bromo-3-isothiazolylmethylthio)ethylamino]-4-pyrimidone
2-[2-(2-amino-5-(1,3,4-thiadiazolyl)methylthio)ethylamino]-4-pyrimidone
2-[5-(4-imidazolyl)pentylamino]-4-pyrimidone

EXAMPLE 26

2-[2-(4-Methyl-5-imidazolylmethylthio)ethylamino]-5-phenyl-6-methyl-4-pyrimidone When 5-phenyl-6-methylthiouracil is used as the starting material in the procedures of Example 22 the title compound, m.p. 215.5°–217.5° C., is produced.

EXAMPLE 27

| Ingredients | Amounts |
|---|---|
| 2-[2-(4-methyl-5-imidazolylmethylthio)-ethylamino]-4-pyrimidone | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 28

| Ingredients | Amounts |
|---|---|
| 2-[2-(4-Methyl-5-imidazolylmethylthio)-ethylamino]-5-benzyl-6-methyl-4-pyrimidone | 200 mg |
| Lactose | 100 mg |

The ingredients are screened, mixed and filled into a hard gelatin capsule.

What we claim is:

1. A compound of the formula:

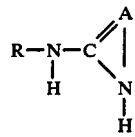

wherein A taken together with the nitrogen and carbon atoms shown forms a pyrimidine ring, said ring having a keto or thione group and optionally substituted on a carbon atom by one lower alkyl, phenyl or benzyl group and optionally by one additional lower alkyl group; R is a grouping of the formula:

$$\text{Het}-CH_2Z(CH_2)_n-$$

wherein Het is an imidazole ring which is attached at a ring carbon and which is optionally substituted by one lower alkyl, amino, hydroxy or halogen; Z is sulphur or a methylene group and n is 2 or 3 or a pharmaceutically acceptable acid addition salt thereof.

2. A compound of claim 1 of the formula:

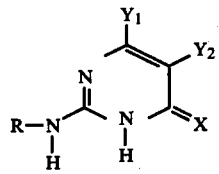

wherein R has the same significance as in claim 1; X is oxygen or sulphur and one of $Y_1$ and $Y_2$ is hydrogen, lower alkyl, phenyl or benzyl and the other is hydrogen or lower alkyl.

3. A compound of claim 1 wherein Het is an imidazole ring, optionally substituted by methyl.

4. A compound of claim 1 wherein n is 2.

5. A compound of claim 1, said compound being 2-[2-(4-methyl-5-imidazolylmethylthio)ethylamino]-4-pyrimidone.

6. A compound of claim 1, said compound being 2-[2-(4-methyl-5-imidazolylmethylthio)ethylamino]-5-ethyl-6-methyl-4-pyrimidone.

7. A compound of claim 1, said compound being 2-[2-(4-methyl-5-imidazolylmethylthio)ethylamino]-5-benzyl-6-methyl-4-pyrimidone.

* * * * *